United States Patent
Holtorf

[19]

[11] Patent Number: 5,983,749
[45] Date of Patent: Nov. 16, 1999

[54] DUAL POSITION FOOT PEDAL FOR OPHTHALMIC SURGERY APPARATUS

[75] Inventor: James L. Holtorf, Thousand Oaks, Calif.

[73] Assignee: Allergan Sales, Inc., Irvine, Calif.

[21] Appl. No.: 08/928,091

[22] Filed: Sep. 12, 1997

[51] Int. Cl.[6] .............................. G05G 1/14; G05G 9/00
[52] U.S. Cl. ................. 74/560; 74/478; 74/512
[58] Field of Search .................. 74/560, 562, 562.5, 74/478, 478.5, 512, 539, 542; 200/86.5

[56] References Cited

U.S. PATENT DOCUMENTS

| | | | |
|---|---|---|---|
| 4,067,522 | 1/1978 | Williams | 200/86.5 X |
| 4,168,707 | 9/1979 | Douvas et al. . | |
| 4,837,857 | 6/1989 | Scheller et al. | 74/512 X |
| 4,933,843 | 6/1990 | Scheller et al. . | |
| 4,965,417 | 10/1990 | Massie | 74/512 X |
| 4,983,901 | 1/1991 | Lehmer . | |
| 5,091,656 | 2/1992 | Gahn . | |
| 5,268,624 | 12/1993 | Zanger . | |
| 5,422,521 | 6/1995 | Neer et al. | 200/86.5 X |
| 5,635,777 | 6/1997 | Telymonde et al. | 200/86.5 X |

FOREIGN PATENT DOCUMENTS

| | | |
|---|---|---|
| 0085518 | 8/1983 | European Pat. Off. . |
| WO9302627 | 2/1993 | WIPO . |

*Primary Examiner*—Tamara L. Graysay
*Assistant Examiner*—Brandon C. Stallman
*Attorney, Agent, or Firm*—Walter A. Hackler

[57] ABSTRACT

A dual position foot pedal includes a base and pedal arrangement which enables access by one of the user's toe and a user's sole for manipulation of the pedal. Switching between the two pedal positions is achieved by rotating the pedal. In this manner, the foot pedal combines the functionality of two common surgical foot pedal types in one pedal.

10 Claims, 7 Drawing Sheets

DUAL POSITION FOOT PEDAL FOR OPHTHALMIC SURGERY APPARATUS

The present invention generally relates to operating controls for ophthalmic surgical apparatus and more particularly to foot operated controls.

Ophthalmic surgical apparatus such as phacoemulsification apparatus typically include operating controls for regulating parameters or functions of the apparatus. Such phacoemulsification apparatus is particularly directed for surgically removing the natural, crystalline lenses from cataractic eyes prior to the insertion of an artificial intraocular lens.

Such apparatus typically includes a control cabinet, power supply, vacuum pump as well as associated electronic hardware for operating a multifunction handheld surgical implement in order to sonically emulsify eye tissue, irrigate the eye with a saline solution and aspirate the emulsified lens from the eye.

In view of the handheld instrumentation necessary for a phacoemulsification procedure, foot controls are frequently provided in order to facilitate use of the handpiece by delegating other control functions to the foot pedal device.

Any number of foot pedal device systems have been utilized which included a variety of pneumatic and electrical actuators to control the ophthalmic surgical apparatus.

Improved foot pedal control systems, such as that described in U.S. Pat. No. 4,983,901 provide for a virtually unlimited number of control variations and modes for operating phacoemulsification apparatus.

However, despite the output from such foot pedals in regulating or controlling the apparatus, the pedal must be user friendly in order to provide a surgeon comfort and reliability in its use so as not to initiate disruption of the surgeon's concentration when performing surgery.

As may be expected, different types of foot pedals are preferred by various surgeons, with some surgeons preferring an accelerator type pedal in which the sole of the surgeon's foot is utilized for depression, while others desire a pedal engageable by the surgeon's toe in order to depress the pedal.

This, of course, leads to the development of a multitude of foot pedal devices of diverse configuration in order to provide the comfort and reliability desired by individual surgeons.

Unfortunately, when phacoemulsification apparatus is utilized by a number of physicians, a change in foot pedals is often required, which is often inconvenient and may require recalibration of the apparatus. In addition, such alternative foot pedals may not be or available/offered by a manufacturer.

Thus, it is desirable to provide a foot pedal apparatus which can be utilized by all attending physicians despite their preference for toe or sole activated pedals. The present invention fulfills that need.

SUMMARY OF THE INVENTION

A dual position foot pedal in accordance with one embodiment of the present invention generally includes a pedal, a base, and a means for rotatably mounting the pedal to the base in order to provide access thereto by one of the user's toe and a user's sole for manipulation of the pedal.

More particularly, the pedal may have a toe end and a heel end and a mounting plate may be provided along with means for pivotably attaching the pedal to the mounting plate at the pedal heel end.

In addition, the means for rotatably mounting the pedal may further include swivel means for attaching the mounting plate to the base.

Importantly, the swivel means includes means for supporting the mounting plate at an angle to the base in order to provide a change in elevation of the toe end of the pedal to facilitate depression thereby by either the sole of a user's foot or the toe of the user's foot.

To facilitate this operation, a heel rest extension plate may be provided and slideably disposed in the base. The slidable heel rest extension therefore provides for accommodating not only for different sizes, but to provide a comfortable position for the user.

In addition, index means may be provided and disposed on the base for releasably engaging the mounting plate to prevent rotation with the toe end or heel end of the pedal aligned with the heel rest extension. More particularly the index means may include a foot accessible lever for enabling engagement and disengagement of the index means with the mountable plate. In this manner, the foot pedal may be adjusted and changed in configuration for toe depression or sole depression with such configuration change being effected by the user's foot alone. That is no manipulation is necessary with the user's hand.

Further, the foot pedal may include at least one foot activated switch and means disposing the foot activated switch adjacent the pedal for enabling actuation of the foot activated switch by lateral displacement of the user's foot depressing the pedal. Further, the present invention may encompass the use of two foot activated switches with means disposing one of the foot activated switches on adjacent sides of the pedal and moveable therewith, for enabling actuation of the foot activated switches by lateral displacement of the user's foot depressing the pedal.

Another embodiment of the present invention provides for a dual position foot pedal including a base, a pedal including both means for receiving a user's sole and means for receiving user's toe with the means for receiving user's sole being spaced apart from the means for receiving the user's toe. A means is provided for pivotably attaching the pedal to the base.

By separately providing means for receiving a user's sole and a user's toe the pedal enables the use by positions despite their preference for toe or sole activated pedals.

Particularly, the means for receiving a user's sole comprises a flat plate disposed at an angle to the base and the means for receiving the user's toe comprises a roller disposed in a parallel relationship with the flat plate. The roller may be disposed intermediate the base and an elevated end of the flat plate.

In addition, at least one foot actuates switch lever may be provided and disposed adjacent to both the flat plate and the lower for enabling actuation of the switch lever by lateral displacement of the user's foot when the user's sole engages the flat plate and when the user's toe engages the roller. A heel rest extension plate, slideably disposed in the base and extending outwardly from the base, provides a means for enabling heel support when the user's toe engages the roller.

BRIEF DESCRIPTION OF THE DRAWINGS

The advantages and features of the present invention will be better understood by the following detailed description when considered in conjunction with the accompanying drawings in which.

DETAILED DESCRIPTION

Figure 1:
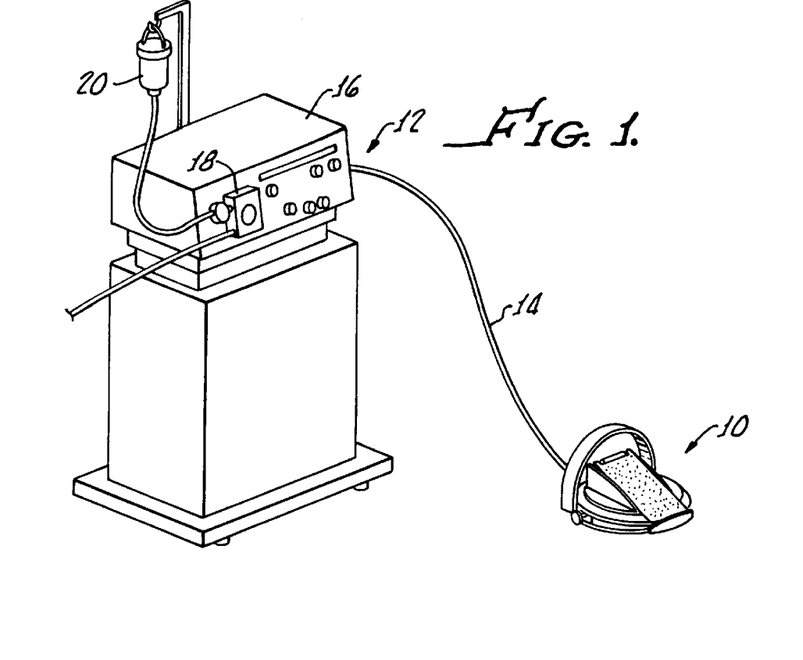
FIG. 1 is a perspective view of a rotatable foot pedal in accordance with one embodiment of the present invention as it may be connected with ophthalmic surgery apparatus.

Turning now to FIG. 1, there is shown a dual position foot pedal 10 in accordance with the present invention connected with ophthalmic surgical apparatus 12 by means of a line 14. Although not part of the present invention, the apparatus 12 may include the console 16 for controlling phacoemulsification procedures which may include a cassette 18 removably disposed therein for controlling fluid flow of, for example, saline solution, shown in a supported container 20.

Various inputs may be provided to the console 16 through the line 14 as is well known in the art. The line 14 may be electrical or pneumatic for transmitting information from the foot pedal 10 to the console 16 as is also well known in the art.

Figure 2:
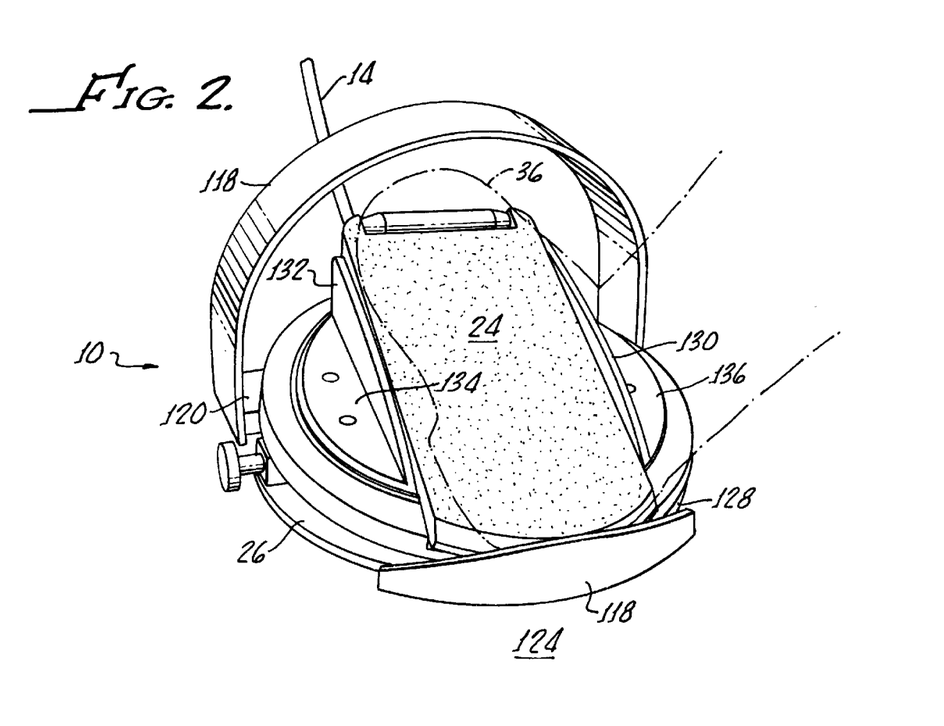
FIG. 2 is an enlarged perspective view of the foot pedal illustrated in FIG. 1 showing operation thereof by a user's sole.
Figure 3:
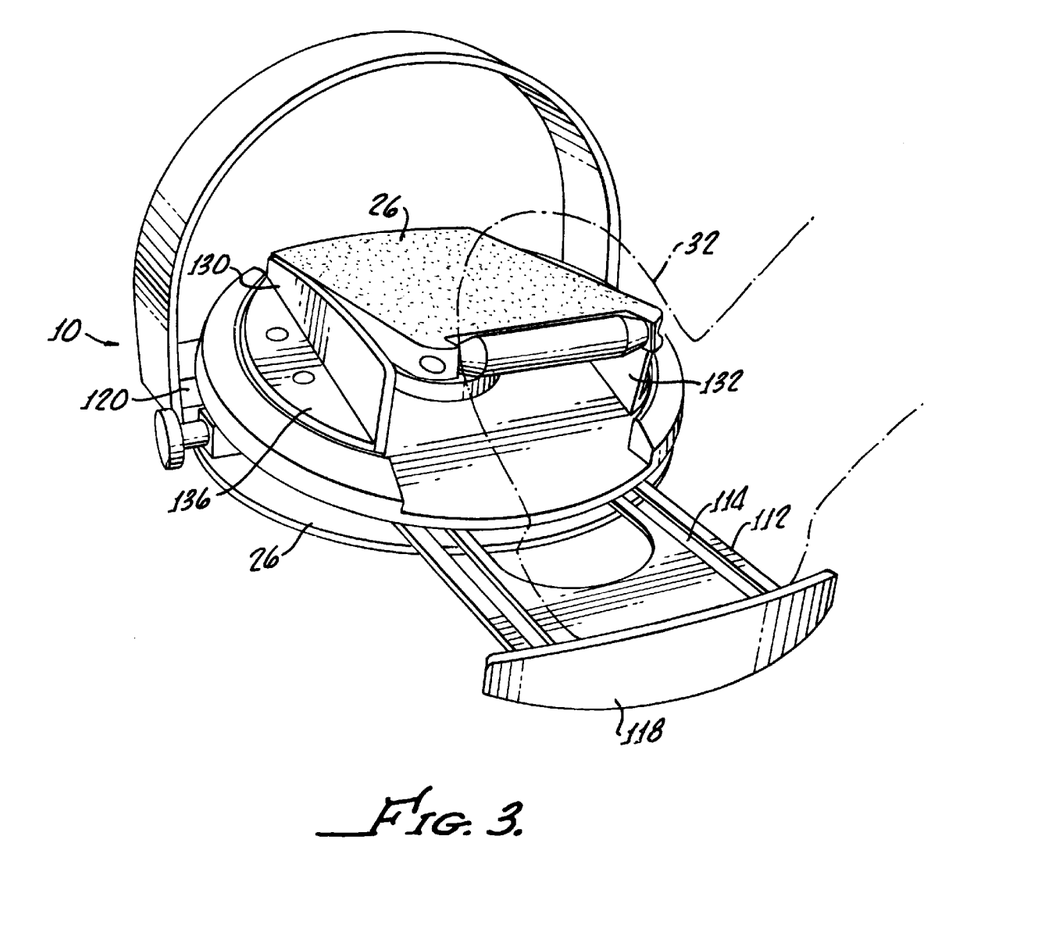
FIG. 3 is a perspective view of the foot pedal in accordance with the one embodiment of the present invention when rotated for actuation by a user's toe.
Figure 4:
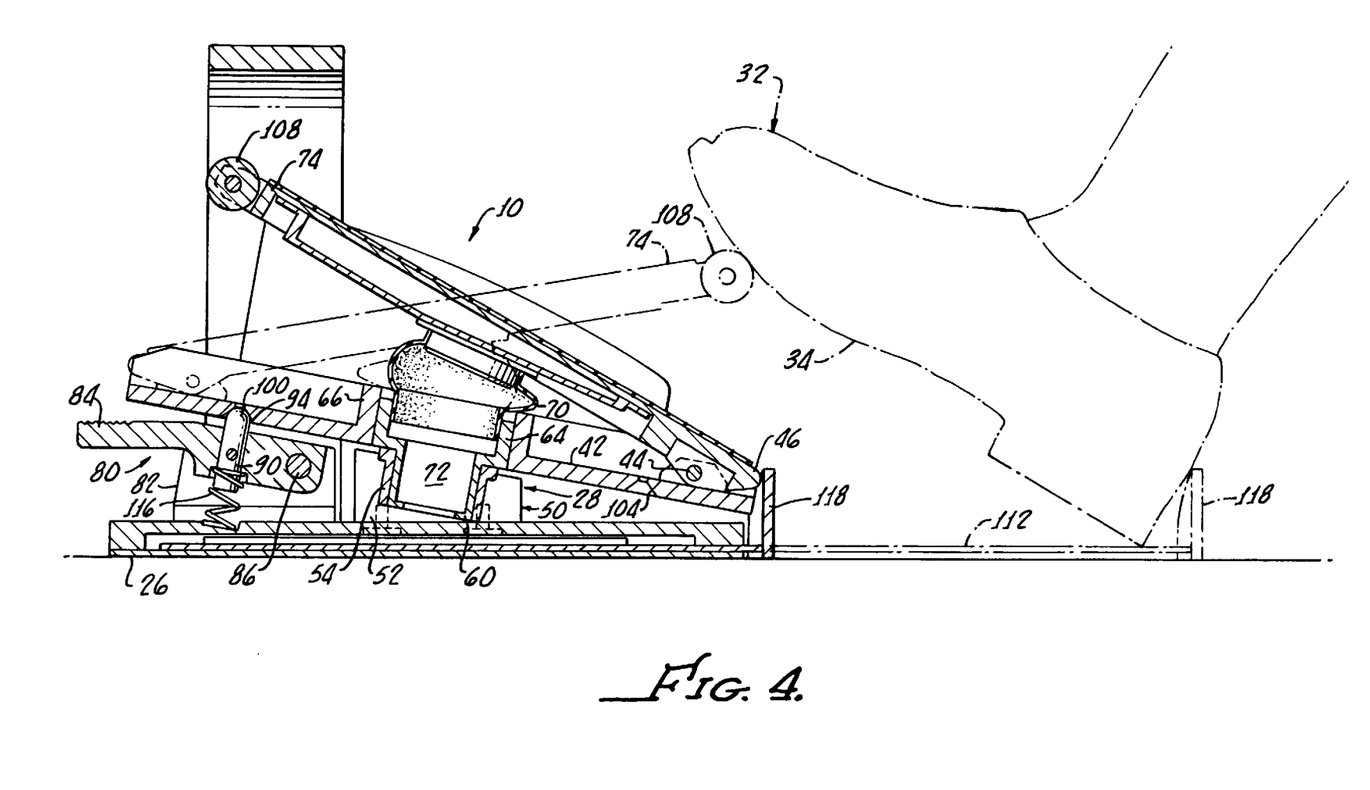
FIG. 4 is a cross sectional view of the one embodiment of the present invention, in solid line, the foot pedal rotated for activation by a user's sole and, in broken line, the foot pedal rotated for actuation by a user's toe, shown in broken line.

Turning now to FIGS. 2 and 3, the foot pedal 10 in accordance with the present invention includes a pedal 24, a base 26 and means 28 for rotatably mounting the pedal 24 to the base in order to provide access thereto by one of the user's toe 32, (see FIGS. 3 and 4) or the sole, or bottom, 34 of the user's foot 36, (see FIGS. 2 and 4). More specifically, as shown in FIG. 4, the means 28 includes a mounting plate 42 and a hinge 44 for pivotably attaching the pedal 24 to the mounting plate 42 at one end 46 of the pedal 24.

In addition, a swivel 50 provides a means for attaching the mounting plate 42 to the base 26 with the swivel 50 including a mounting bracket 52 having a bearing 54 for accepting a cylinder 60 attached to the pedal 42 through an upper portion 64 fitted into upstanding portion 66 of the pedal 42.

It should be appreciated that all of the components hereinbefore and hereinafter noted which form a part of the foot pedal in accordance with the present invention may be formed and made from any suitable material and configured for operating in the manner herein described.

A collapsible diaphragm 70 is provided between the foot pedal 24 and the mounting plate 42 in order to provide a closed space 72 therebetween for supporting an actuating mechanism, not shown, which may be electrical or pneumatic for providing a signal related to the amount of the depression of the foot pedal 24 to the console 16 via the line 14. It should be appreciated that any type of mechanism may be used in combination with the present invention which provides an output corresponding to pedal 24 depression.

The bracket 52 provides a means for supporting the mounting plate 42 at an angle to the base 26. This is important since it enables the mounting plate 42 to raise and lower a toe end 74 of the pedal 24 as may be clearly discerned by comparing the broken line position of the pedal 24 and the solid line position of the pedal 24 as shown in FIG. 4.

In order to temporarily lock the foot pedal 24 in a position for engagement by a user's sole, shown in solid line in FIG. 4, or a user's toe 32 shown in broken line in FIG. 4, index means 80 are provided and attached to the base 26 by a bracket 82.

A foot accessible lever 84 is hinge 86 mounted to the bracket 82 includes a pin 90 biased into a notch 94 by a spring 96. It is apparent in FIG. 4 that depression of the foot lever 84 compresses the spring 96 and withdraws an end 100 of the pin 90 from the notch 94 allowing rotation of the mounting plate 42 and pedal 24 until the pin end 100 is received in a notch 104 in the mounting plate 42 which facilitates access to the toe end 74 of the pedal 24 by the user's toe 32. A bumper 108 may be provided for facilitating engagement of the toe end 74 of the foot pedal 24 with the user's toe 32 which may have a textured surface or other accommodation for facilitating non slip contact with the user's toe 32.

Figure 5:
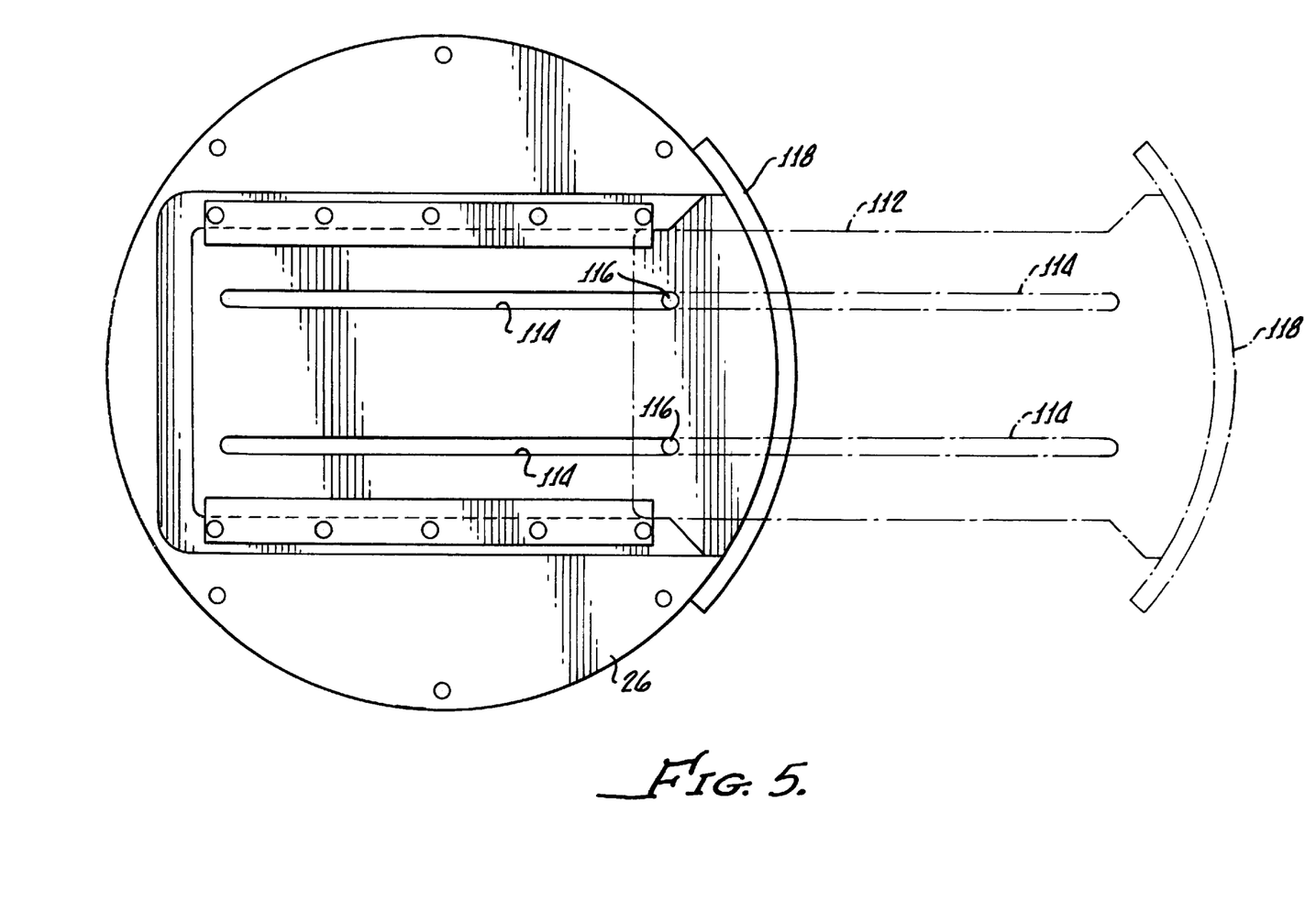
FIG. 5 is a plan view of the base of the foot pedal of FIG. 4 showing, in solid line, a heel rest contained within a base of the foot pedal and, in broken line, the heel rest in an extended position for accommodating the heel of a user at a position enabling toe contact with the pedal.

In addition, a heel rest extension plate 112, as also shown in FIG. 5, may be slideably disposed in the base 26, slots 114 in the extension plate 112 receiving pins 116 fixed in the base 26 for enabling the plate 112 to slide into a closed position, shown in solid line in FIG. 5, to an open position, shown in broken line in FIG. 5. A heel piece 118 connected to the heel rest extension plate 112 and upstanding therefrom provides support for a user's heel, as shown in FIGS. 3 and 4 to prevent slippage of the user's foot 36 while pressing the pedal 26. A friction fit between the slots 114 and pins 116 enables the heel rest extension plate 112 to be adjustably withdrawn from the base to provide for different user foot 36 sizes and preferences in foot position while depressing the foot pedal 26. To facilitate placement of the foot pedal 10, a bracket, or hoop 118 may be fixed to a bracket 120 attached to the base 126 in order to facilitate manual displacement of foot pedal 10 from one position on a floor 124.

In addition the hoop 118 may prevent accidental depression of the pedal 24 or accidental interference with the user's foot 36 when the foot pedal apparatus 10 is in use.

As shown in FIGS. 2 and 3, lateral foot switch levers 130, 132 may be provided and disposed on the mounting plate 42 adjacent the pedal 26 by means of angle brackets 134, 136.

The switch levers 130, 132 may be connected to conventional switches, not shown, for providing addition control signals, as may be desired, to the console 12.

Hence the foot pedal in accordance with the present invention combines the functionality of two common surgical foot pedal types into one pedal, namely a -heel activated- and -toe activated- operating foot pedal.

Switching between the two pedal 26 options is achieved by simply rotating the mounting plate 42 with the foot pedal 24 attached thereto 180° about the swivel 50. In this operation the base 26, which may be a heavy stabilizing structure, can remain in place. As hereinabove described the pedal 26 may be locked into either position by the index means 80.

The maximization of foot pedal angle for each mode is achieved by virtue of the mounting of the plate 42 at an angle with the base 26.

The operating foot pedal range for the heel activated mode is approximately 25° to 10° with the pedal pivot point under the heel of 128 of the user, see FIG. 2. The operating foot pedal range for toe activated mode, see FIG. 3, is approximately from 5° to −10° with the pivot point approximately 6 inches in front of toe 32, the pivot point being established by the heel rest 118. Thus, the foot pedal apparatus in accordance with the present invention provides operating ranges which maximize the ergonomics of each pedal type.

Figure 6:
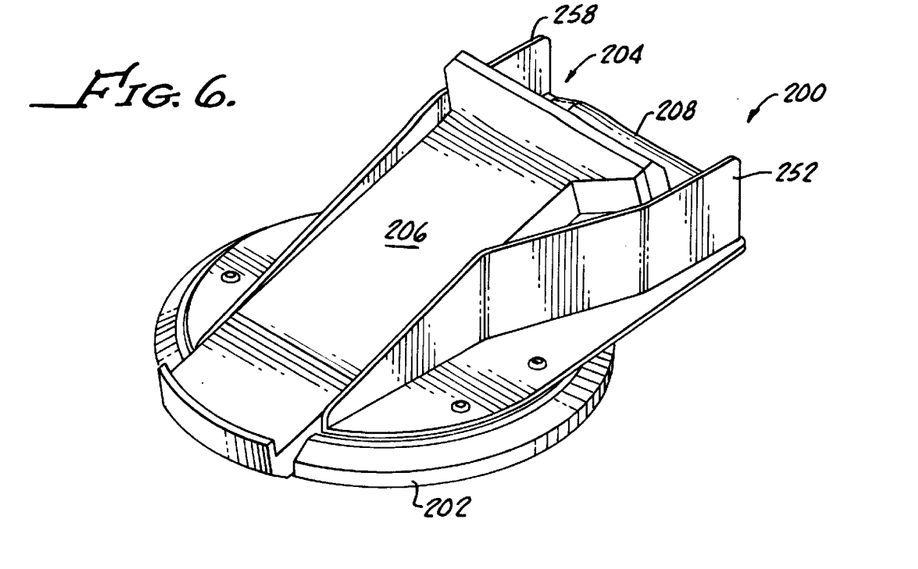
FIG. 6 is a perspective view of another embodiment of the present invention in an orientation for operation by a user's sole.
Figure 7:
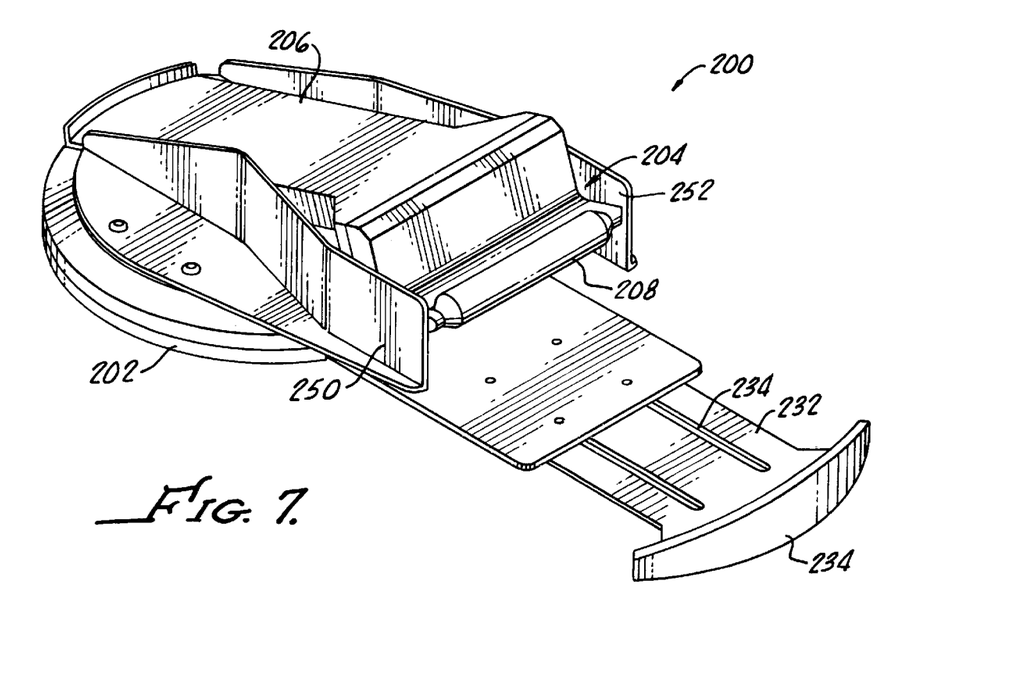
FIG. 7 is a perspective view of the embodiment shown in FIG. 6 in an orientation suitable for use by a user's toe.

Turning now to FIGS. 6 and 7 there is shown another embodiment of a dual position foot pedal 200 in accordance with the present invention which generally includes a base 202 and a pedal 204. Pedal 204 includes a flat plate 206 which provides means for receiving a user's sole 222 (See FIG. 8) which is disposed at an angle to the base 202. In addition, pedal 204 includes a roller 208, disposed in a parallel relationship with the flat plate 206, which provides means for receiving a user's toe 224.

Figure 8:
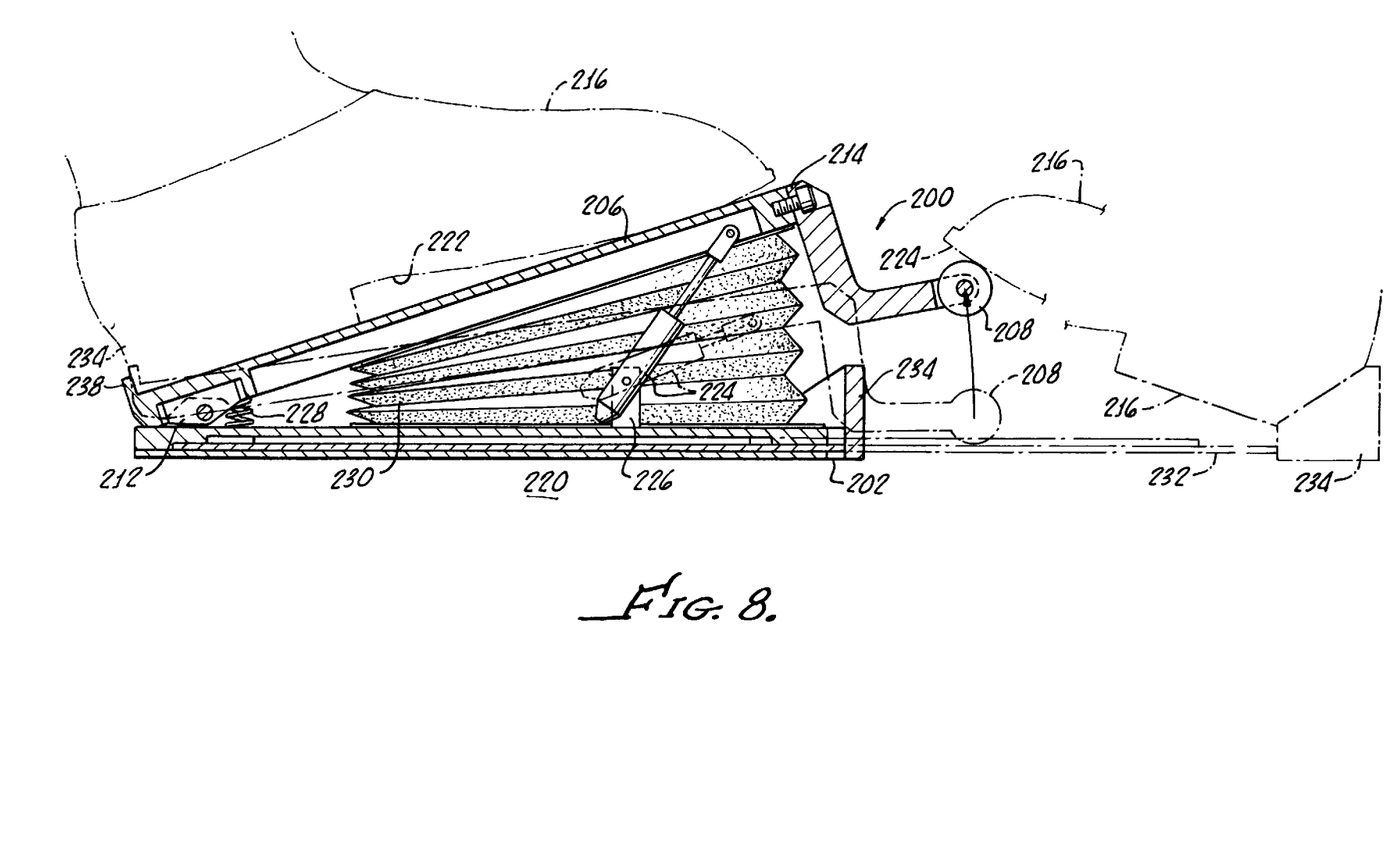
FIG. 8 is a cross sectional elevation view of the embodiment shown in FIGS. 6 and 7.
Figure 9:
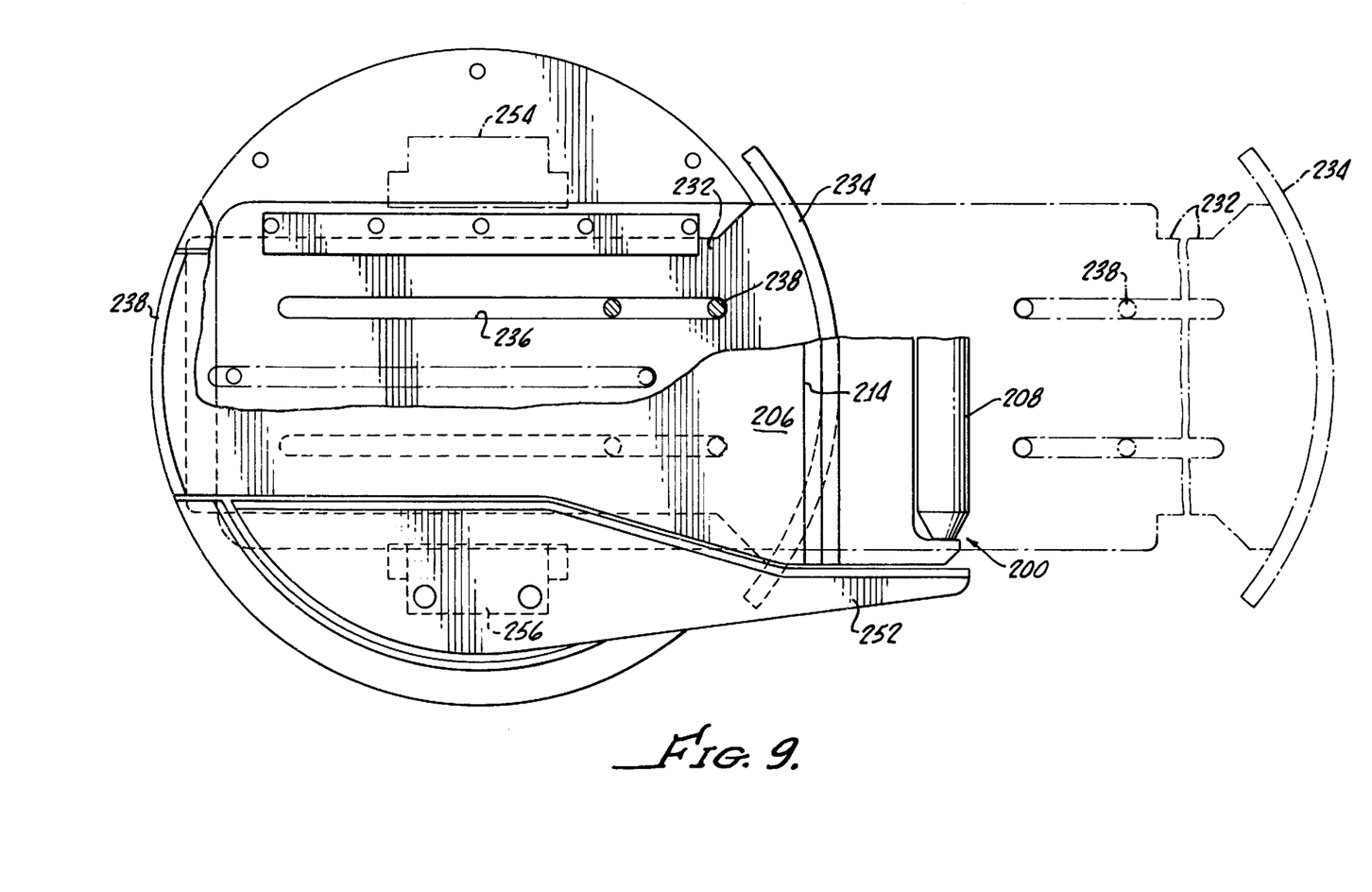
FIG. 9 is a cross sectional plane view of the embodiment shown in FIGS. 6 and 7, showing, in solid line, a heel rest contained within a base of the foot pedal and, in broken line, the heel rest in an extended position for accommodating the heel of a user at a position enabling toe contact with the pedal.

As shown in FIG. 8 a hinge 212 provides a means for pivotably attaching the pedal 206 to the base 202. As is most clearly shown in FIG. 8, the roller 208 is disposed intermediate the base 202 and an elevated end 214 of the flat plate 206 which enables toe access and proper angular relationship with a user's foot 216 shown in broken line in FIG. 8. Thus, the foot pedal 200 need only be repositioned on a supporting floor 220 to enable access by a user's sole 222 contacting the flat plate 206 or the user's toe 224 contacting the roller 208. Resilience of the pedal to depression may be provided by springs 228 disposed in operable combination with the hinge 212 or any of the other suitable biasing mechanism. An actuator 224 interconnected between the flat plate 206 and a bracket 226 fixed to the base 202 provides a means for sending a signal to the console 16 corresponding to pedal position, the actuator 224 being of a conventional construction. A diaphragm 230 may be provided for surrounding the actuator 224 to provide isolation from environmental dirt. Similar to the foot pedal embodiment 10 hereinabove described, a heel rest extension plate 232 shown in FIGS. 7, 8 and 9 which is slideably disposed in the base 206 and extendible outwardly from the base 206 provides a means for supporting a heel 234 when the user's toe 224 engages the roller 208 as also hereinabove described slots 236 and pins 238 enabling sliding movement of the heel 234 extension plate 232.

Similar support for the user's heel 234 using the flat plate 206 for depression is provided by an upstanding portion 240 around the flat plate 206.

Turning back to FIGS. 6 and 7, similar to the embodiment 10, hereinabove described, lateral foot switch levers 250, 252 may be provided and disposed adjacent a flat plate 206 and roller 208 by means of brackets 254,256 in a conventional manner for enabling actuation thereof by lateral displacement of the user's foot 216 when the user's sole 222 engages the flat plate 206 and also when the user's toe 224 engages the roller 208. The switch levers 250,252 may be connected to conventional switches, not shown, for providing additional control signals as may be desired to the console 12.

Although there has been hereinabove described a specific arrangements of a dual position foot pedal in accordance with the present invention, for the purpose of illustrating the manner in which the invention may be used to advantage, it should be appreciated that the invention is not limited thereto. Accordingly, any and all modification, variations, or equivalent arrangements which may occur to those skilled in the art, should be considered to be within the scope of the present invention as defined in the appended claims.

What is claimed is:

1. A dual position foot pedal comprising:
    a pedal;
    a base;
    means for rotatably mounting said pedal to said base in order to provide access thereto by one of a user's toe and a user's sole for manipulation of said pedal, the mounting means including a mounting plate, means for pivotally attaching said pedal to said mounting plate at one end of said pedal, and swivel means for attaching said mounting plate to said base, said swivel means comprising means for supporting said mounting plate at an angle to a heel rest extension plate slidably disposed in said base.

2. The foot pedal according to claim 1 further comprising index means disposed on said base for releasably engaging said mounting plate to prevent rotation thereof.

3. The foot pedal according to claim 2 wherein said index means includes foot accessible lever means for enabling engagement and disengagement of the index means with said mounting plate.

4. The foot pedal according to claim 2 further comprising at least one foot activated switch lever and means disposing the foot activated switch lever adjacent said pedal for enabling activation of the foot activated switch lever by lateral displacement of a user's foot depressing said pedal.

5. The foot pedal according to claim 2 further comprising two foot activated switch levers and means disposing one of the foot activated switch levers adjacent sides of said pedal and moveable therewith, for enabling activation of the foot activated switch levers by lateral displacement of user's foot depressing said pedal.

6. A dual position foot pedal comprising:
    a pedal having a toe end and a heel end;
    a mounting plate;
    means for pivotally attaching said pedal to said mounting plate at the pedal heel end;
    a base;
    swivel means for attaching said mounting plate for 18020 rotation with respect to said base in a manner enabling a change in height of the pedal toe end upon 180° rotation of the mounting plate, said height being measured from the toe end to the base, said swivel means comprising means for supporting said mounting plate at an angle to said base; and
    a heel rest extension Plate slidably disposed in said base.

7. A dual position foot pedal comprising:
    a pedal having a toe end and a heel end;
    a mounting plate;
    means for pivotally attaching said pedal to said mounting plate at the pedal heel end;
    a base;
    swivel means for attaching said mounting plate for rotation with respect to said base in a manner enabling a change in height of the pedal toe end upon rotation of the mounting plate, said height being measured from the toe end to the base; and
    index means disposed on said base for releasably engaging said mounting plate to prevent rotation with one of the toe end and heel end of the pedal aligned with a heel rest extension.

8. The foot pedal according to claim 7 wherein said index means includes foot accessible lever means for enabling engagement and disengagement of the index means with said mounting plate.

9. The foot pedal according to claim 7 further comprising at least one foot activated switch lever and means disposing the foot activated switch lever adjacent said pedal for enabling activation of the foot activated switch lever by lateral displacement of a user's foot depressing said pedal.

10. The foot pedal according to claim 7 further comprising two foot activated switch levers and means disposing one of the foot activation switch levers adjacent sides of said pedal and moveable therewith, for enabling activation of the foot activated switch levers by lateral displacement of a user's foot depressing said pedal.

* * * * *

UNITED STATES PATENT AND TRADEMARK OFFICE
CERTIFICATE OF CORRECTION

PATENT NO : 5,983,749
DATED : November 16, 1999
INVENTOR(S): James L. Holtorf

It is certified that error appears in the above-identified patent and that said Letters Patent is hereby corrected as shown below: Column 6, line 1-16, Claim 1, 1. A dual position foot pedal comprising:

a pedal;

a base;

means for rotatably mounting said pedal to said base in order to provide access thereto by one of a user's toe and a user's sole for manipulation of said pedal, the mounting means including a mounting plate, means for pivotally attaching said pedal to said mounting plate at one end of said pedal, and swivel means for attaching said mounting plate to said base, said swivel means comprising means for supporting said mounting plate at an angle to said base; and     a heel rest extension plate slidably disposed in said base.

Signed and Sealed this

Twenty-third Day of May, 2000

Attest:

Attesting Officer

Q. TODD DICKINSON

Director of Patents and Trademarks